(12) United States Patent
Cheiky et al.

(10) Patent No.: US 8,372,311 B2
(45) Date of Patent: *Feb. 12, 2013

(54) PROCESS FOR BIOMASS CONVERSION TO SYNTHESIS GAS

(75) Inventors: Michael Cheiky, Thousand Oaks, CA (US); Rajashekharam Malyala, Camarillo, CA (US); Ronald A. Sills, Houston, TX (US)

(73) Assignee: Cool Planet Biofuels, Inc., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,522

(22) Filed: Mar. 23, 2012

(65) Prior Publication Data

US 2012/0286211 A1 Nov. 15, 2012

Related U.S. Application Data

(63) Continuation of application No. 13/103,922, filed on May 9, 2011, now Pat. No. 8,173,044.

(51) Int. Cl.
*C01B 3/28* (2006.01)
*C01B 3/24* (2006.01)

(52) U.S. Cl. ........................ 252/373; 423/650
(58) Field of Classification Search .................... 252/373
See application file for complete search history.

(56) References Cited

U.S. PATENT DOCUMENTS

| 203,016 | A | 4/1878 | Edison |
|---|---|---|---|
| 222,390 | A | 12/1879 | Edison |
| 474,230 | A | 5/1892 | Edison |
| 4,268,275 | A | 5/1981 | Chittick |
| 4,421,524 | A | 12/1983 | Chittick |
| 4,487,958 | A | 12/1984 | Ream et al. |
| 4,497,637 | A | 2/1985 | Purdy et al. |
| 4,530,702 | A | 7/1985 | Fetters et al. |
| 4,861,351 | A | 8/1989 | Nicholas et al. |
| 4,992,480 | A | 2/1991 | Mahajan et al. |
| 5,032,618 | A | 7/1991 | Marchionna et al. |
| 5,087,786 | A | 2/1992 | Nubel et al. |
| 5,221,290 | A | 6/1993 | Deil |
| 5,504,259 | A | 4/1996 | Diebold et al. |
| 5,756,194 | A | 5/1998 | Shogren et al. |
| 5,820,640 | A | 10/1998 | Ikura et al. |
| 5,857,807 | A | 1/1999 | Longo |
| 6,133,328 | A | 10/2000 | Lightner |
| 6,227,473 | B1 | 5/2001 | Arnold |
| 6,339,031 | B1 | 1/2002 | Tan |

(Continued)

FOREIGN PATENT DOCUMENTS

| KR | 100819505 | 3/2008 |
|---|---|---|
| WO | WO 2009004652 | 1/2009 |

OTHER PUBLICATIONS

Z. Rosenberg; "More on Commercial Carbon Resistors as Low Pressure Guages," Intl. Jour, of Impat Eng, 34 (2007) pp. 732-742.

(Continued)

*Primary Examiner* — Melvin C Mayes
*Assistant Examiner* — Kenneth Vaden
(74) *Attorney, Agent, or Firm* — Sheppard Mullin Richter & Hampton LLP

(57) ABSTRACT

Biomass is processed through a biomass fractioning system that creates, through the application of selective temperature ramps and pressure shocks, a series of useful volatile components and BMF char, wherein the BMF char is reacted sacrificially with any one stream of methane, carbon dioxide, steam or oxygen to create highly pure synthesis gas with a controllable range of compositions. The resulting synthesis gas may be used in any desired manner, including conversion to oxygenates such as methanol and dimethyl ether, and to hydrocarbons.

20 Claims, 10 Drawing Sheets

U.S. PATENT DOCUMENTS

| | | | |
|---|---|---|---|
| 6,548,026 | B1 | 4/2003 | Dales et al. |
| 6,747,067 | B2 | 6/2004 | Melnichuk et al. |
| 6,811,703 | B2 | 11/2004 | Elliott |
| 6,841,085 | B2 | 1/2005 | Werpy et al. |
| 6,923,838 | B2 | 8/2005 | Maubert et al. |
| 6,994,827 | B2 | 2/2006 | Safir et al. |
| 7,033,972 | B2 | 4/2006 | Shikada et al. |
| 7,226,566 | B2 | 6/2007 | Beierle |
| 7,458,999 | B2 | 12/2008 | Schenck et al. |
| 7,846,979 | B2 | 12/2010 | Rojey et al. |
| 7,888,540 | B2 | 2/2011 | Deluga et al. |
| 2003/0119952 | A1 | 6/2003 | Werpy et al. |
| 2004/0111968 | A1 | 6/2004 | Day et al. |
| 2008/0006519 | A1 | 1/2008 | Badger |
| 2008/0093209 | A1 | 4/2008 | Noto |
| 2008/0216391 | A1 | 9/2008 | Cortright et al. |
| 2008/0223269 | A1 | 9/2008 | Paoluccio |
| 2008/0300435 | A1 | 12/2008 | Cortright et al. |
| 2008/0317657 | A1 | 12/2008 | Hall et al. |
| 2009/0007484 | A1 | 1/2009 | Smith |
| 2009/0139139 | A1 | 6/2009 | Tilman et al. |
| 2009/0151251 | A1 | 6/2009 | Manzer et al. |
| 2009/0183430 | A1 | 7/2009 | Schubert et al. |
| 2009/0217575 | A1 | 9/2009 | Raman et al. |
| 2009/0253947 | A1 | 10/2009 | Brandvold et al. |
| 2009/0308787 | A1 | 12/2009 | O'Connor et al. |
| 2010/0040510 | A1 | 2/2010 | Randhava et al. |
| 2010/0162780 | A1 | 7/2010 | Scharf |
| 2010/0180805 | A1 | 7/2010 | Cheiky |
| 2010/0218417 | A1 | 9/2010 | Bauldreay et al. |
| 2010/0223839 | A1 | 9/2010 | Garcia-Perez et al. |
| 2010/0257775 | A1 | 10/2010 | Cheiky |
| 2010/0270505 | A1 | 10/2010 | Gallaspy et al. |
| 2010/0300866 | A1 | 12/2010 | Van Aardi et al. |
| 2011/0023566 | A1 | 2/2011 | Lodwig et al. |
| 2011/0177466 | A1 | 7/2011 | Cheiky |

OTHER PUBLICATIONS

R Buerschaper, "Thermal & Electrical Conductivity of Graphite & Carbon at Low Temperatures," Jour. of App. Physics; (1994) pp. 452-454.

I.M. Lima, "Physiochemical & Adsorption Properties of Fast-Pyrolysis Bio-Chars & their Steam Activated Counterparts," J. Chem. Biotechnical (2010) 85, pp. 1515-1521.

Cheng. CHih-Hsin; "Stability of Black Carbon in Soils Across a Climatic Gradient," Jour. of Geophysical Researth Biogeosciences: 113 (2008) G02027; pp. 1-10.

Lehmann, J.; Nutrient Avai., & Leaching in an Archaeological Anthrosol & Ferraisol of the Central Amazon Basin: Fertilizer. Manure.; Plant Soil 249 (2003); pp. 343-357.

Preston, C.M.: (Pyrogenic) Carbon: a Synthesis of Curent Knowledge & Uncertainties w/Special Consideration of Boreal Regions; Biogeosciences 3 (2006); pp. 397-420.

Tryon, E.H.; "Effect of Charcoal on Certain Physical, Chemical, & Biological Properties of Forest Coils," Ecological Monoraphs, vol. 18, No. 1 (Jan. 1948), pp. 81-115.

Faludi, J.; "World Changing Change Your Thinking a Carbon-Negative Fuel:" Oct. 16, 2007; www.worldchanging.com.

Laird; David; "The Charcoal Vision: A Win Win Scenario," 2008. Agron, J., vol. 100, No. 1, pp. 178-181.

Ogawa "Carbon Sequestration by Carbonization of Biomass & Forestaion; 3 Case Studies," Mitigation & Adaption Strategies for Global Change, vol. 11 (2006), pp. 429-444.

Demirbas, "Effects of Temperature & Particle Size on Bio-Char Yield from Pyrolysis of Agricultural Residues." J. Anal. Pyrolysis, vol. 72 (2004); pp. 243-248.

Kim et al.: Characteristics of Crosslinked Potato Starch & Starch-Filled Linear Low-Density Polyethylene Films, Carbohydrate Polymers, vol. 50 (2002); pp. 331-337.

Norman, et al.; "Best Management Practices for Reclaiing Surface Mines in Washington and Oregon," Open-File Report 0-92-2, revised ed. Dec. 1997; www.oregongeology.org Feb. 9, 2010.

E. Gegver & K. Hayek; "A Fully Programmable System for the Study of Catalytic Gas Reactions," 1985 J. Physc. E: Sci. Instrum. 18 836.

D.C. Elliott "Liquid Fuels by Low-Severity Hydrotreating of Biocrude," Dev. in Thermochemicai Biomass Conversion; vol. 1, pp. 611-621.

Dinesh Mohan, "Pyrolysis of Wood/Biomass for Bio-Oil: A Critical Review," Energy & Fuelds (2006): 20, pp. 848-889.

Ramesh K. Sharma: "Catalytic Upgrading of Pyrolysis Oil," Energy & Fuels (1993), 7, pp. 306-314.

Thiam Leng Chew, "Catalytic Processes Towards the Production of Biofuels in a Palm Oil and Oil Palm Biomass-based Biorefinery," Biorefinery, Bioresource Tech. 99 (2008), pp. 7911-8922.

K. Omata; "Optimization of Cu Oxide Catalyst for Methanol Synthesis under High C02 Partial Pressure Using Combinatorial Tools," App. Catalyst A: General 262 (2004), 207-214.

Kaoru Takeishi: "Dimethy Ether & Catalyst Development for Production Syngas," Biofuels (2010) 1 (1), pp. 217, 226.

PROCESS FOR BIOMASS CONVERSION TO SYNTHESIS GAS

CROSS REFERENCE TO RELATED APPLICATIONS

This application is a continuation of prior application Ser. No. 13/103,922, filed May 9, 2011, now U.S. Pat. No. 8,173,044, the contents of which are hereby incorporated in its entirety.

TECHNICAL FIELD

The present invention relates generally to systems for making renewable fuels, and more particularly to the conversion of char generated using a reactor to produce highly pure synthesis gas that can ultimately generate value added chemicals and renewable fuels.

DESCRIPTION OF THE RELATED ART

The planet is warming and solutions are being sought to decrease the magnitude of this effect. Global temperatures are expected to increase by at least 2 degrees Celsius by the middle of the century. The rise of global temperatures is expected to produce significant disruptions to the global ecosystem and to the lives of millions of individuals across the planet. Processes that reduce carbon emissions in a significant manner are urgently needed. The Fischer-Tropsch process converts a mixture of carbon monoxide and hydrogen (synthesis gas) into hydrocarbons of varying numbers of carbon, which can then be upgraded to diesel, gasoline, aviation fuel, lubricants and chemicals. A Fischer-Tropsch process that utilizes renewable sources as feedstock is highly desired to achieve global carbon emissions reductions. Synthesis gas can also be converted in another processing route to emerging fuels methanol and dimethyl ether (DME), which can be converted to gasoline. As long as the synthesis gas that is used in the process is derived from a renewable resource, this process may have an important effect in controlling carbon emissions.

Present Fischer-Tropsch or methanol processes rely on different feedstock of varying degrees of quality, that is mostly derived from either the steam reforming of natural gas or from the gasification of coal. Fischer-Tropsch projects generally consist of synthesis gas generation, Fischer-Tropsch synthesis and product upgrading. A problem with these approaches is that the synthesis gas produced from coal and the natural gas feedstock for steam reforming has high impurities (particularly sulfur-containing compounds), or requires complicated and expensive equipment to clean impurities in the produced synthesis gas. These impurities derive from the source methane or the source coal. High purity synthesis gas is desired due to the extreme sensitivity of Fisher-Tropsch catalysts to impurities such as sulfur and chloride.

Present Fischer-Tropsch or methanol processes rely on synthesis gas with a desired hydrogen to carbon monoxide ($H_2$/CO) ratio. The preferred $H_2$/CO ratio for the Fischer-Tropsch process is about 2. Synthesis gas obtained directly from steam methane reforming has an excess of hydrogen. Synthesis gas obtained directly from coal gasification is deficient in hydrogen. Therefore, the $H_2$/CO ratio must be adjusted using complicated and expensive equipment. The present approach allows adjustment of the ratio of hydrogen to carbon monoxide by varying the source and quantity of reactants.

Various forms of laboratory and small scale commercial biomass pyrolyzers have been developed to generate useful chemical products from the controlled pyrolysis of biomaterials ranging from wood chips to sewage sludge. Although some pyrolyzers are focused simply on producing synthesis gas, there is considerable effort in the development of milder pyrolyzing conditions, which typically results in a condensed liquid commonly known as bio-oil or pyrolysis oil. Many forms of pyrolyzers have been developed at the laboratory level to produce these intermediate compounds, which are collectively referred to as bio-oil or pyrolysis oil. Configurations include simple tube furnaces where the biomass is roasted in ceramic boats, ablative pyrolyzers where wood is rubbed against a hot surface, various forms of fluidized bed pyrolyzers where biomass is mixed with hot sand, and various simpler configurations that are based on earlier coking oven designs.

The fundamental problem with the resultant pyrolysis oil is that it is made up of hundreds to thousands of compounds, which are the result of subjecting the raw biomass to a wide range of temperature, time, and pressure profiles in bulk. When this process is complicated by the thousands of major bio-compounds in the original bio-feedstock, the result is a nearly intractable array of resultant compounds all mixed together. Char (also referred to as bio-char) is also produced in the mix. Pyrolysis oils from such processes are typically not thermodynamically stable. They contain active oxygenated free radicals that are catalyzed by organic acids and bases such that these oils typically evolve over a period of a few days from light colored liquids to dark mixtures with tar and resinous substances entrained in the mix. Also, attempts to re-gasify pyrolysis oil typically result in additional chemical reactions, which produce additional biochar and a shift to lower molecular weight components in the resulting gas stream. Although fairly high yields of pyrolysis oil can be achieved in laboratory scale experiments, larger industrial scale demonstration projects typically produce much lower yield. This is presumably due to the wider range of temperatures, hold times, and localized pressures within the much larger heated three dimensional volumes of such scale-up architectures. Thus the pyrolysis oil is not stable enough nor the biochar is pure enough for further processing without needing complicated and expensive equipment to remove impurities in the synthesis gas.

The production and reactions of charcoal have been known since the start of the industrial revolution. The following discussion is limited to synthesis gas production from biomass. There exist several approaches to the production of synthesis gas from biomass. U.S. Pat. No. 6,133,328 discloses a method whereby biomass is decomposed with stored hot air to incandescent carbon at 1000° C. The hot air is cutoff and steam is introduced to react with the carbon to produce hydrogen and carbon monoxide. Additional steam is introduced to react with the exiting carbon monoxide to carbon dioxide and additional hydrogen, thereby bringing the ratio of $H_2$/CO to 2.0. U.S. Pat. No. 4,497,637 discloses the conversion of biomass to synthesis gas via a system that pyrolyzes biomass with pyrolysis oil and preheated air. Char, pyrolysis oil and pyrolysis gas are generated. Pyrolysis gas is diverted to dry the incoming biomass, while the char and pyrolysis oil are gasified with steam and oxygen to produce synthesis gas.

U.S. Pat. No. 7,226,566 teaches a method of producing fuel and charcoal from biomass that entails an apparatus comprised of a multistage reaction chamber, a biomass delivery system, a charcoal removal system, a fuel gas removal system, filter, pump, demister, heat exchanger, and fuel storage. The upper level of the reaction chamber embodies the biomass input, the middle layer includes a pyrolysis region generating synthesis gas and water vapor, and the lower level comprises a charcoal bed. The system is said to be a one-container system for the production of fuel from biomass. Similar concepts are expressed in U.S. Pat. Nos. 4,268,275, 4,421,524 and 4,530,702.

U.S. Pat. No. 6,747,067 by Melnichuk et al teaches a method of generating synthesis gas from biomass in which cellulosic feedstock is continuously fed into a heated vessel between 675° C. and 900° C. in the absence of oxygen. The heated vessel receives a continuous infusion of steam which cracks said cellulose feedstock into fly ash, carbon, carbon monoxide and hydrogen. The carbon particulates are mechanically removed and reacted with steam at 400-500° C. and 3-15 atmospheres to cause a water gas shift. Korean Patent 100819505 teaches a unified system for steam reforming tar and soots to synthesis gas that uses large diameter biomass gasifiers.

U.S. Patent Application Nos. 2010/0270505 and 2009/0151251 disclose pyrolyzing a carbon containing feedstock to form a pyrolyzed feed stream such as char, which is then converted to synthesis gas, typically via a water shift reaction. U.S. Patent Application No. 2009/0183430 teaches a system for the production of synthesis gas from biomass utilizing a means for compacting the biomass, removing air from said biomass during the compaction, and heating the biomass at sufficiently high temperatures (greater than 950° C.) to create synthesis gas and ash. No char is said to be formed.

Synthesis gas is typically obtained from steam reforming of methane. Methane reformation requires apparatus for feedstock purification to reduce sulfur and chloride levels which easily poison the catalyst. After reformation, in order to obtain product components of high purity, separation or additional processes are often instituted after these components have been formed. There is usually a step to separate the hydrogen from CO and $CO_2$. There is yet another step to separate CO from $CO_2$. Thus U.S. Pat. No. 4,861,351 discloses a hydrogen product of 98+% purity after having selectively adsorbed CO and $CO_2$ with different sorbents. Other methods rely on cryogenic separation of $CO_2$. U.S. Pat. No. 7,846,979 discloses the use of a biomass feedstock to generate synthesis gas and $CO_2$. The $CO_2$ is recycled by reacting with a hydrogen-rich mixture obtained from steam reformation to produce CO and $H_2O$. In this manner synthesis gas with a ratio of $H_2/CO$ of 2.15 is obtained.

BRIEF SUMMARY OF EMBODIMENTS OF THE INVENTION

The above-described methods of generating synthesis gas from bio-char differ substantially from the methods of the invention, which utilize a novel type of char referred as biomass fractionated (BMF) char. The BMF char may be generated according principles disclosed in co-filed U.S. patent application Ser. No. 13/103,905 entitled "Method for Biomass Fractioning by Enhancing Thermal Conductivity." BMF char is generated in a unique manner using a biomass fractioning reactor in which biomass is fractioned into thin sheets, and the thin sheets are subject to specific temperature ramps and pressure shocks.

According to various embodiments of the invention, the adjustment of synthesis gas ratio is unique in that it is controlled by the nature and quantity of the feedstock. Depending on whether the feedstock is hydrogen-rich or oxygen-rich, a wide spectrum of synthesis gas compositions may be obtained.

Another embodiment features a method for producing synthesis gas from biomass, comprising: grinding a biomass feedstock to produce ground biomass particles; dispensing the ground biomass particles into thin sheets; subjecting the thin sheets of ground biomass to a treatment including sequential or concurrent ramps of temperature and pressure shocks; and recovering a residual non-volatile biomass component from the treatment and reacting the component with at least one of methane, oxygen, steam, and carbon dioxide, at high temperatures.

An additional embodiment involves a method for adjusting the ratio of hydrogen to carbon monoxide in synthesis gas, comprising: grinding a biomass feedstock to produce ground biomass particles having diameters in the range of 0.001 inch to 1 inch; dispensing ground biomass into thin sheets having a thickness that is a multiple of the ground biomass particle diameter; subjecting the ground biomass to sequential or concurrent ramps of temperature and pressure shocks; selectively collecting various groups of volatile compounds as they are released from the biomass; collecting a remaining non-volatile component of the thin sheets; reacting the non-volatile component with one of oxygen, methane, steam, and carbon dioxide; and adjusting a ratio of reacted oxygen, methane, steam, or carbon dioxide to produce synthesis gas having a hydrogen/carbon ratio in a range of 0 to 100.

Embodiments of the invention use a novel type of char created from a biomass fractionator (i.e., BMF char) for the production of high purity synthesis gas.

Further embodiments of the invention use BMF char to create a synthesis gas mixture with a wide composition of hydrogen and carbon monoxide Additional embodiments of the invention are directed toward methods that react vast stores of methane with BMF char to ultimately generate value added chemicals.

Yet further embodiments of this invention are directed toward methods to synthesize gasoline using reactions on BMF char.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present invention is directed toward biomass fractioning, whereby biomass is processed through a biomass fractioning system that creates a series of useful volatile components and BMF char through the application of selective temperature ramps and pressure shocks. In particular, the BMF char is reacted with any one stream of methane, carbon dioxide, steam or oxygen to create highly pure synthesis gas with a controllable range of compositions. The resulting synthesis gas may be used in any desired manner, including conversion to oxygenates such as methanol and dimethyl ether, and to Fischer-Tropsch products such as gasoline, diesel, lubricants and naptha.

Unlike conventional methods that produce synthesis gas having high impurities, embodiments of the invention produce high purity synthesis gas via conversion of BMF char. Additionally, some embodiments allow for the adjustment of the ratio of hydrogen to carbon monoxide by varying the source and quantity of reactants. Further embodiments of the invention employ a novel char that is sufficiently clean to be processed further for high purity synthesis gas production.

BMF Char Generation

Figure 1:
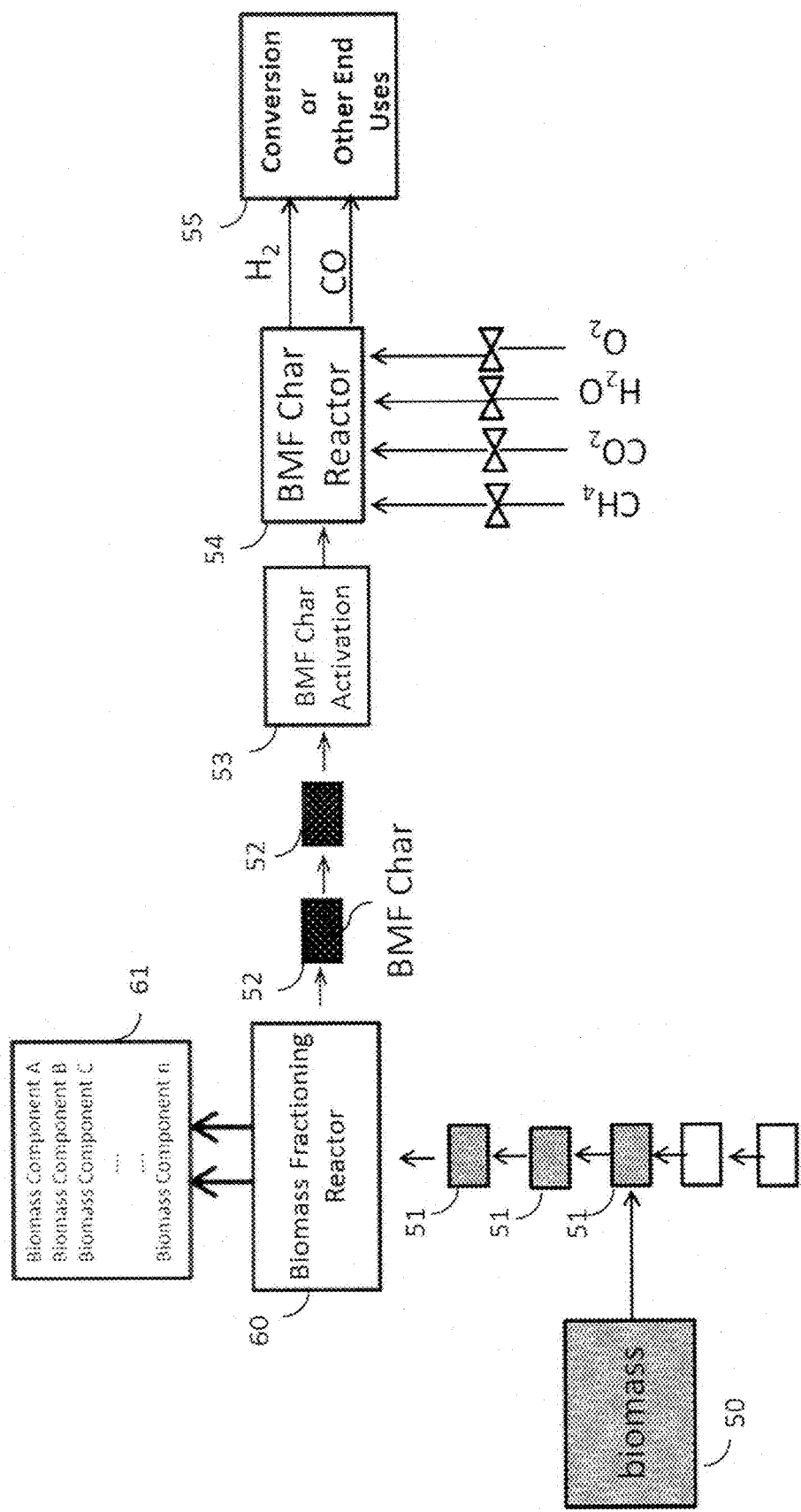
FIG. 1 is a flow diagram showing biomass conversion to BMF char with subsequent reaction in a BMF char reactor.
Figure 2:
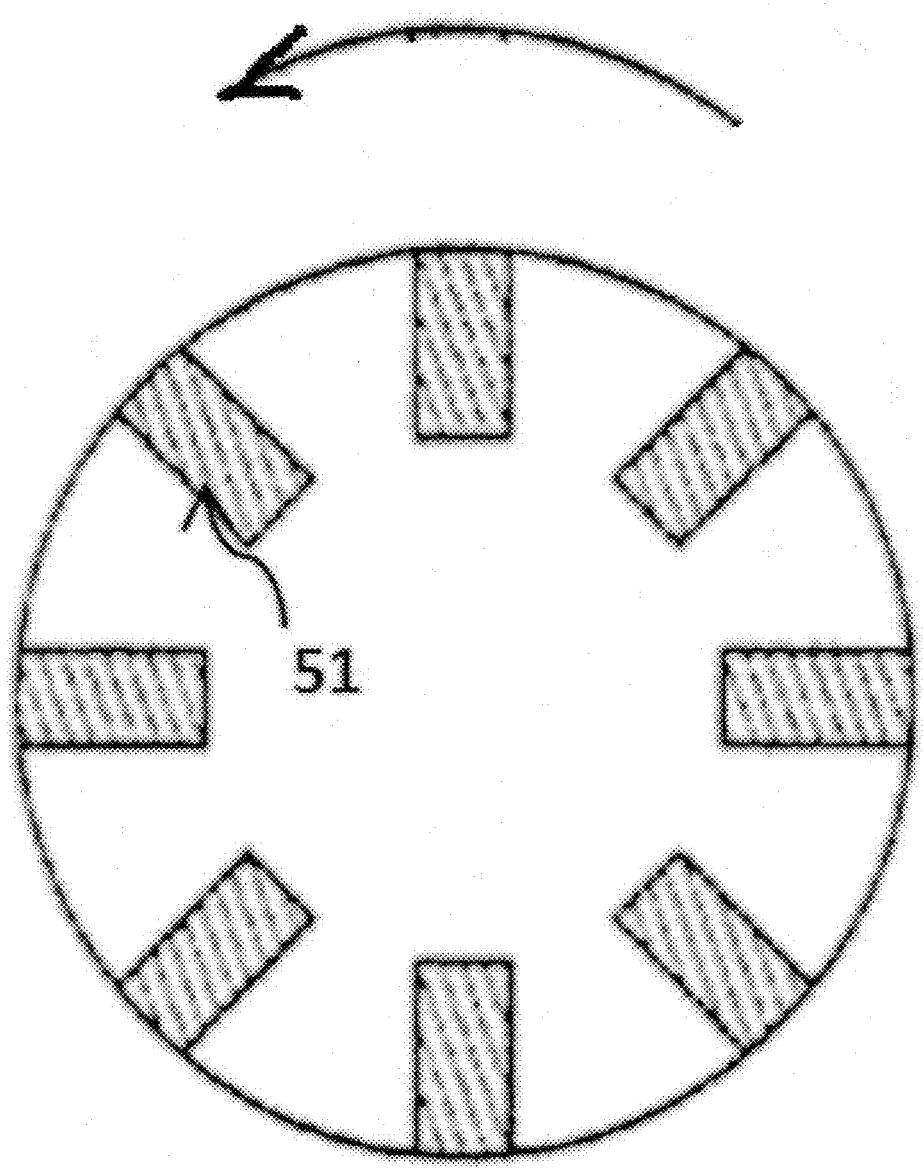
FIG. 2 illustrates an alternate method of loading biomass onto a rotating disc supporting biomass reaction chambers.

Embodiments of the present invention involve synthesis gas production from BMF char. Specifically, this char may be generated following the principles disclosed in co-owned, co-pending U.S. patent application Ser. No. 13/103,905 entitled "Method for Biomass Fractioning by Enhancing Thermal Conductivity," the content of which is incorporated herein by reference in its entirety. The following discussion illustrates the BMF char generation. Referring now to FIG. 1, biomass 50 is loaded piecemeal onto a plurality of movable biomass reaction chambers 51. By way of example, the compartments may be made movable using conventional drive mechanisms such as gear drives, chain drives, ratcheting sprockets, etc. In addition to linear displacements, the reaction chambers 51 may also be arranged on a disc that rotates continuously or in a stepwise fashion as shown in FIG. 2. The biomass 50 is then passed to a biomass fractioning reactor 60 that allows the production of high-yield bio-intermediary compounds 61 and residual char 52 (i.e., BMF char).

As used herein, the term 'biomass' includes any material derived or readily obtained from plant sources. Such material can include without limitation: (i) plant products such as bark, leaves, tree branches, tree stumps, hardwood chips, softwood chips, grape pumice, sugarcane bagasse, switchgrass; and (ii) pellet material such as grass, wood and hay pellets, crop products such as corn, wheat and kenaf. This term may also include seeds such as vegetable seeds, sunflower seeds, fruit seeds, and legume seeds.

The term 'biomass' can also include: (i) waste products including animal manure such as poultry derived waste; (ii) commercial or recycled material including plastic, paper, paper pulp, cardboard, sawdust, timber residue, wood shavings and cloth; (iii) municipal waste including sewage waste; (iv) agricultural waste such as coconut shells, pecan shells, almond shells, coffee grounds; and (v) agricultural feed products such as rice straw, wheat straw, rice hulls, corn stover, corn straw, and corn cobs.

With further reference to FIG. 1, the biomass may be ground by a variety of techniques into a particle size suitable for dispensation into the reaction chamber 51. Particle size may range from 0.001 inch to 1 inch in diameter, limited by processing equipment size and thermal transfer rates.

Embodiments of the invention feature a biomass chamber 51 that is much wider and longer than it is thick. In some cases, biomass is dispensed into thin sheets whose total thickness is 1 to 30 times the biomass particle size. A preferred thickness for the chamber for uncompressed biomass (which is ground or chopped to ⅛" or smaller) is approximately ¾" in thickness. As the biomass is heated and further pulverized (as discussed below), the emerging BMF char quickly condenses to a layer about 1/10" thick. This aspect ratio ensures mild pyrolyzing conditions that allow the collection of useful chemical compounds known as bio-intermediary compounds as well as the production of BMF char. A person of skill in the art will appreciate that these biomass chambers can be sized in width and length along with the diameter of their corresponding drive disc to any such size as appropriate for the desired throughput for the biomass fractionator, without departing from the scope if the invention.

Figure 3:
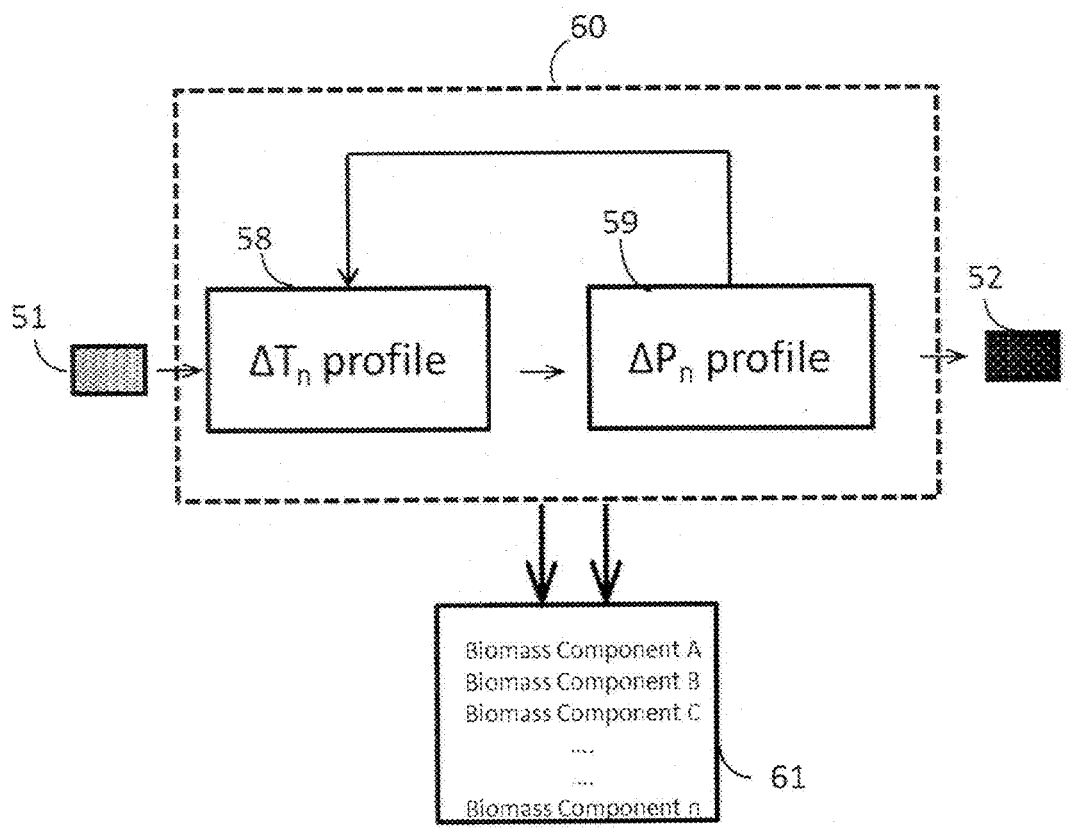
FIG. 3 is a diagram illustrating a process for generating the BMF char.

Referring to FIG. 3, the ground biomass is passed to biomass fractioning reactor 60, which subjects the biomass to a series of temperature ramp profiles ($\Delta T n$) and pressure shock profiles ($\Delta P n$), where n is an integer greater than 1 that describes the stages in the step-wise decomposition of the biomass. In particular, the biomass is subjected first to a heating profile $\Delta T 1$, typically a linear temperature ramp, by a heating agent such as a metal anvil at processing station 58. Typically, the purpose of this first $\Delta T 1$ profile is to dewater the biomass. Subsequent $\Delta T n$ profiles end at progressively higher temperatures and serve the purpose of outgassing and of thermo-chemically converting solid biomass to volatile bio-compounds. These useful bio-compounds with progressively higher devolatilization temperatures. In order to accomplish this devolatilization in a selective manner, the temperature treatment is accompanied by a pressure treatment. In the illustrated embodiment, this is achieved using compacting station 59 (e.g., a series of anvils) for subjecting the biomass to accompanying pressure profiles $\Delta P n$ comprising a sequence of pressure shocks that exploit the inherent compressional features of carbon.

In some embodiments, the temperature profiles are linear ramps ranging from 0.001° C./sec to 1000° C./sec, and preferably from 1° C./sec to 100° C./sec. Processing heating station 58 may be heated by electrical heating elements, direct flame combustion, or by directed jets of heated working gas or supercritical fluid. The heating profile and the pressure compaction profile may be linked via a feedback loop and may be applied by the same agent simultaneously. Compacting station 59 may be controlled by electrically driven devices, air compressed devices, or any other form of energy that serves to impact load the biomass. BMF char 52 remains after these processing steps.

Figure 4:
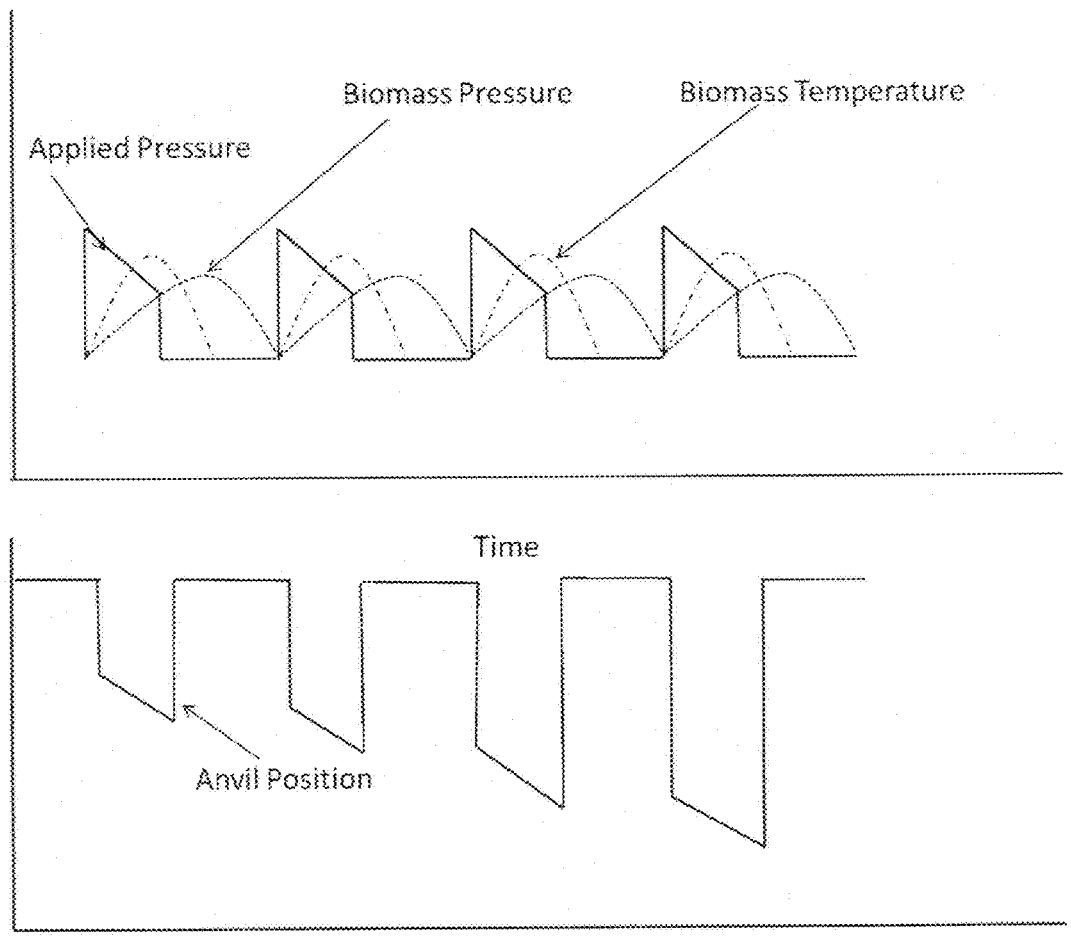
FIG. 4 illustrates an embodiment of applied pressure and temperature and corresponding biomass response.

The selective pyrolysis of the biomass arises out of the interplay between the applied pressure pulses, applied temperature and resultant pressures and temperatures experienced by the biomass. The process is illustrated diagrammatically in FIG. 4, which shows applied pressure, biomass temperature, biomass pressure and anvil position as a function of time. It is understood that a wide variety of different types of pressure pulses may be applied, and that the entire illustration is a pedagogic device. In FIG. 4, pressure shocks applied via compacting station 59 are shown as a series of triangular pressure pulses with an unspecified rest time. The process starts out by utilizing the thermal conductivity of water. The biomass is first subjected to a temperature ramp sufficient to cause the biomass to release water. The released heated water vapor is then subjected to a pressure shock which compresses the steam, thus accelerating the biomass decomposition. It may be possible for the steam to attain supercritical form, though that is not a requirement for the present invention.

With continued reference to FIG. 4, the pressure shock also aids in collapsing the biomass. A short time after peak pressure is applied, the anvil is pushed back by the pressure of extracted volatile compounds. When the volatile compounds are removed along with the steam, pressure within the biomass is decreased suddenly. Biomass temperature rapidly returns to base levels, and the anvil returns to its unextended base position. After the water has been removed entirely from the biomass, the applied temperature causes hot localized areas within the biomass that initiate carbon formation. Compressive impacts on the newly formed carbon serve in turn to increase the thermal conductivity of the carbon. The increased thermal conductivity serves to efficiently transmit heat energy needed to break down the biomass to the next stage in its decomposition. Furthermore, because carbon exhibits compressional memory, compressive impacts are sufficient to exert this effect on thermal conductivity.

The compressional memory of carbon has been indirectly demonstrated in studies of commercial carbon resistors as low pressure gauges. See Rosenberg, Z. et al *International Journal of Impact Engineering* 34 (2007) 732-742. In these studies, metal discs were launched from a gas gun at high velocity and impact an epoxy or Plexiglas target in which a carbon resistor is embedded. Resistance changes were measured as a function of time after impact. It was noted that the resistance decreased rather rapidly in less than a microsecond, and stayed low for several microseconds, in some cases over 10 microsecond's, until it began to increase gradually to pre-impact levels. There is essentially a memory effect or a slow relaxation after the impact. As electrical resistance and thermal conductivity are inversely correlated for carbon as for metals (See, for example, Buerschaper, R. A. in *Journal of Applied Physics* 15 (1944) 452-454 and *Encyclopedia of Chemical Technology, 5th edition*), these studies reveal a compression memory on the part of the carbon. This compression memory is at least partly utilized in embodiments of the invention.

Embodiments of the invention also utilize the increase in thermal conductivity as carbon is compressed. The change in electrical resistance with pressure in carbon microphones is a well-known effect utilized by carbon telephones and carbon amplifiers. U.S. Pat. No. 203,016, U.S. Pat. No. 222,390 and U.S. Pat. No. 474,230 to Thomas Edison, describe apparatus that transform sound compressions (vibrations) to changes in electrical resistance of carbon granules. Carbon is even more sensitive than most metals in its inverse relationship between electrical resistance and thermal conductivity. Below are data indicating the thermal conductivity of various substances (CRC Handbook of Chemistry and Physics, 87th edition) in comparison to the measured thermal conductivity of BMF char:

TABLE 1

| Select Thermal Conductivities in W/(m · K) | |
|---|---|
| Copper | 390 |
| Stainless Steel | 20 |
| Water | 0.6 |
| Dry Wood | 0.3 |
| Fuels | 0.1 to 0.2 |
| Carrier Gases ($H_2$, $N_2$, etc.) | 0.01 to 0.02 |
| Carbon Char | 0.01 to 0.05 |
| BMF char | 1 to 5 |

As the thermal conductivity of the formed carbon within the biomass increases due to pressure shocks, it becomes consequently easier to attain mild pyrolysis conditions within the biomass. As higher temperatures are reached, the fact that carbon is a better heat transfer agent than water enables higher boiling compounds to become volatile. Pressure shocks serve to compress these higher boiling compounds and contribute to fracturing cell walls within the biomass. The process is illustrated by FIG. 4 which shows anvil extension at peak pressure getting longer with subsequent pulse application, thus indicating successive biomass pulverization in conjunction with release of useful higher boiling compounds.

A variety of pressure profiles $\Delta Pn$ are effective in increasing the carbon thermal conductivity. The magnitude of the pressure can vary from 0.2 MPa to 10 GPa and may be applied via a number of different technologies, including air driven pistons, hydraulically driven pistons, and explosive driven devices. The duration of the pressure application can vary from 1 microsecond to 1 week. It is understood that pressure pulses of different magnitudes and different time durations may be admixed to yield optimum results.

The efficient heat energy transfer executed by embodiments of the present invention can be enhanced by the addition of supercritical fluids in the reaction chamber. It is known that supercritical fluids can improve heat transfer as well as accelerate reaction rates. Certain embodiments can operate with supercritical carbon dioxide, supercritical water, supercritical methane, supercritical methanol, or mixtures of the above. It is possible that supercritical conditions are created internally with some pressure and temperature profiles.

A system capable of embodying the methods of the present invention is described in co-owned, co-pending U.S. Patent Application No. 2010/0180805 entitled "System and Method for Biomass Fractioning," the content of which is incorporated herein by reference in its entirety. This system comprises a biomass load and dump station, a heated pulverizing processing station for compressing the biomass, a biochar dumping station for removing residual biochar, and a plurality of biomass reaction compartments able to carry the biomass from station to station.

Figure 5:
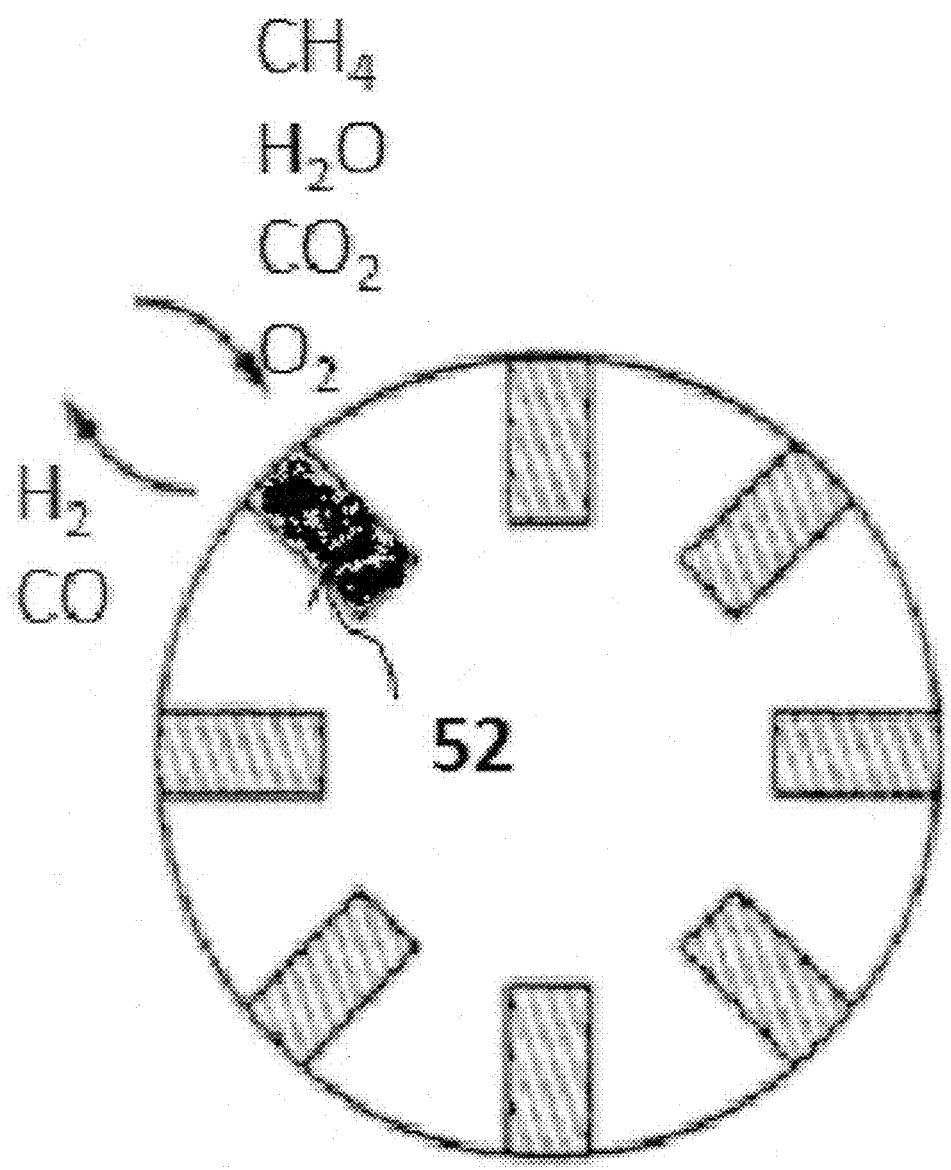
FIG. 5 illustrates an embodiment in which a BMF char reaction chamber is located within a rotating disc.
Figure 6:
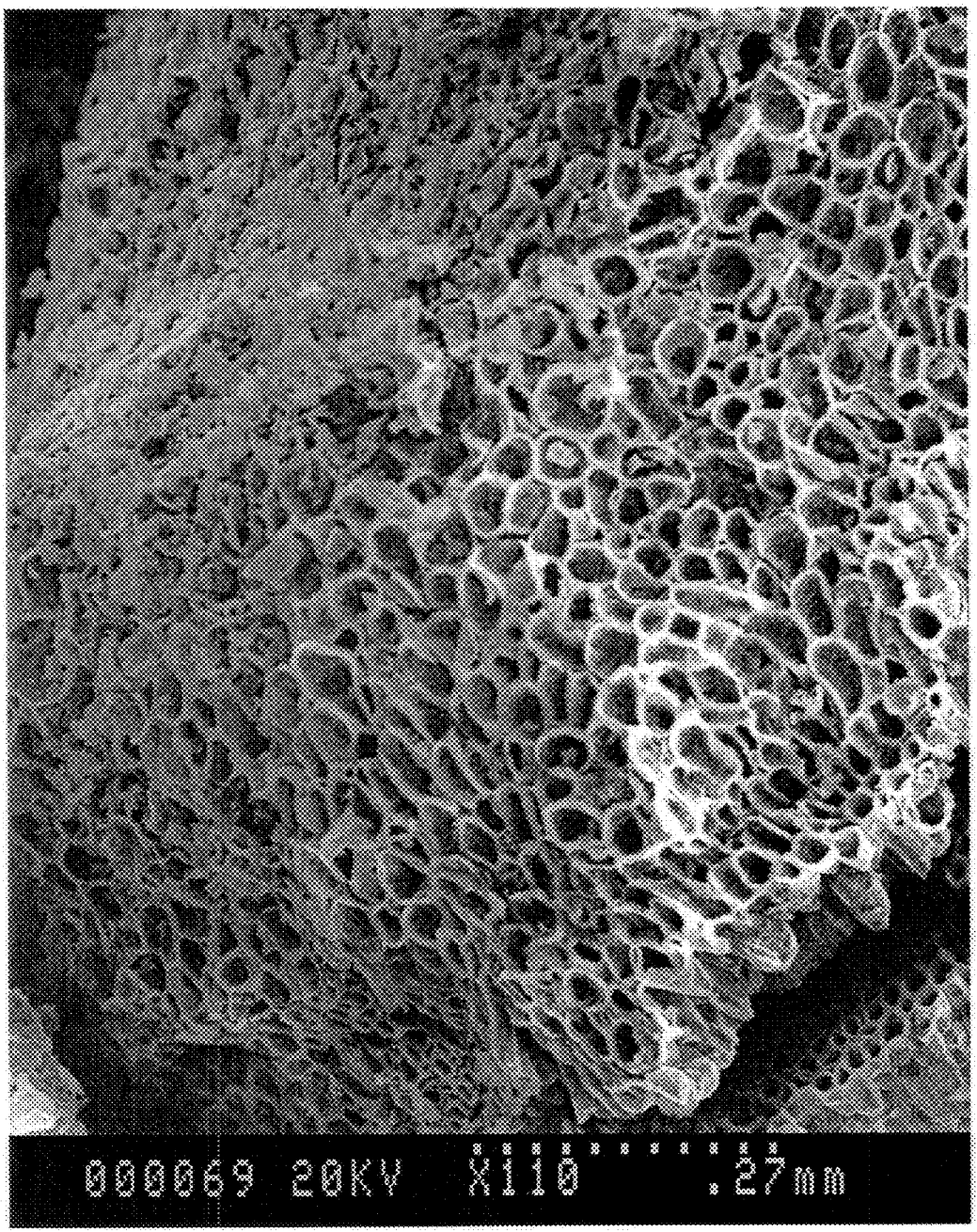
FIG. 6 is a scanning electron microscope (SEM) image of BMF char from corn after its formation.

After the BMF char is formed, it may be reacted in situ as shown in FIG. 5, or it may be optionally transferred as shown in FIG. 1 to a subsequent activation chamber 53 prior to being dispensed into a BMF char reactor 54. The transfer may be accomplished via any number of conventional mechanical means such as a press bar outfitted with a scraping knife. BMF char formed from this process is different than carbonaceous deposits formed from pyrolyzers or coke from petroleum plants, since it exhibits greater thermal conductivity while maintaining high surface area. A scanning electron microscope (SEM) image of BMF char after formation is shown in FIG. 6.

BMF Char Activation

The BMF char is preferably activated prior to use. Activation is a well-known procedure for increasing char surface area and adsorptive capabilities. See, for example, discussion by Lima, I. M. et al, in *Journal of Chemical Technology and Biotechnology*, vol. 85, (2010), pp. 1515-1521. The activation step is an optional pretreatment and selective combustion step which aims to create additional surface area to accelerate subsequent desired reactions. Typical activating agents include $CO_2$, $H_2O$ and $O_2$. Table 2 shows data acquired using different activation agents at 900° C. for BMF char generated using a biomass fractioning reactor. In the case, the BMF char was derived from corn cobs.

The increased surface area of the BMF char upon activation comes at the expense of loss of material, which serves to create a porous structure within the char. Whether exposed to oxygen or methane and air, a loss of approximately 40% of the initial weight was measured. Activation procedures can produce surface areas in excess of 500 $m^2/g$.

TABLE 2

Effect of Activating Agent on BMF Char

| Char Source | Activation Agent | Activation Time | Activation Temp ° C. | BMF Char Loaded, g | Activated BMF Char, g |
|---|---|---|---|---|---|
| Corn Cobs | $O_2$ | 3 Hours | 900 | 47.5 | 29 |
| Corn Cobs | $CH_4$, air | 3 Hours | 900 | 46 | 29.5 |

BMF Char Reactions

BMF char can be reacted in char reactor 54 with one of $CH_4$, $H_2O$, $CO_2$ and $O_2$ as illustrated by the reactions:

$$C + CH_4 \rightarrow 2H_2 + 2C \quad \Delta H° = 75 \text{ kJ/mol} \quad [1]$$

$$C + H_2O \rightarrow CO + H_2 \quad \Delta H° = 132 \text{ kJ/mol} \quad [2]$$

$$C + CO_2 \rightarrow 2CO \quad \Delta H° = 172 \text{ kJ/mol} \quad [3]$$

$$C + \tfrac{1}{2}O_2 \rightarrow CO \quad \Delta H° = -110 \text{ kJ/mol} \quad [4]$$

Equation 1 may be more appropriately written as:

$$C_{BMF} + CH_4 \rightarrow 2H_2 + C_{BMF} + C_{methane} \quad [1a]$$

Thus the carbon in equations 2, 3, and 4 may represent either BMF carbon or carbon from methane, or both.

Any one of the above gaseous reactants with the BMF char may be introduced in supercritical form for faster kinetics. The oxygen concentration should be controlled to avoid complete oxidation of the char as:

$$C + O_2 \rightarrow CO_2 \quad \Delta H° = -393 \text{ kJ/mol} \quad [5]$$

The first three reactions are endothermic, while the fourth is exothermic. The energy for the first three reactions can come from channeling internal heat generated from the fourth reaction or from external sources, e.g., combustion of coal or natural gas, or electricity during off-peak hours. In principle, the heat generated from creating 2 moles of CO via the fourth reaction can be used to power the first three reactions. The following reactions are also relevant for this discussion:

$$H_2O + CO \rightarrow H_2 + CO_2 \quad \Delta H° = -41 \text{ kJ/mol} \quad [6]$$

$$CH_4 + \tfrac{3}{2}O_2 \rightarrow CO2 + 2H_2O \quad \Delta H° = -802 \text{ kJ/mol} \quad [7]$$

$$CH_4 + \tfrac{1}{2}O_2 \rightarrow CO + 2H_2 \quad \Delta H° = -35 \text{ kJ/mol} \quad [8]$$

$$CH_4 + H_2O \rightarrow CO + 3H_2 \quad \Delta H° = 207 \text{ kJ/mol} \quad [9]$$

Equation 1 in particular deserves notice for allowing vast stores of methane to be converted to hydrogen. Present methane reformation on coal produces synthesis gas contaminated with sulfur, since the coal typically contains a few percent by weight of sulfur. The sulfur in the synthesis gas causes catalyst poisoning, and it is removed from the synthesis gas before introducing the latter into a catalyst bed. This represents extra cost and complexity, particularly for small scale modular plants. According to embodiments of the invention, the BMF char is actually cleaner than the incoming methane, leading to high purity synthesis gas.

Figure 7A:
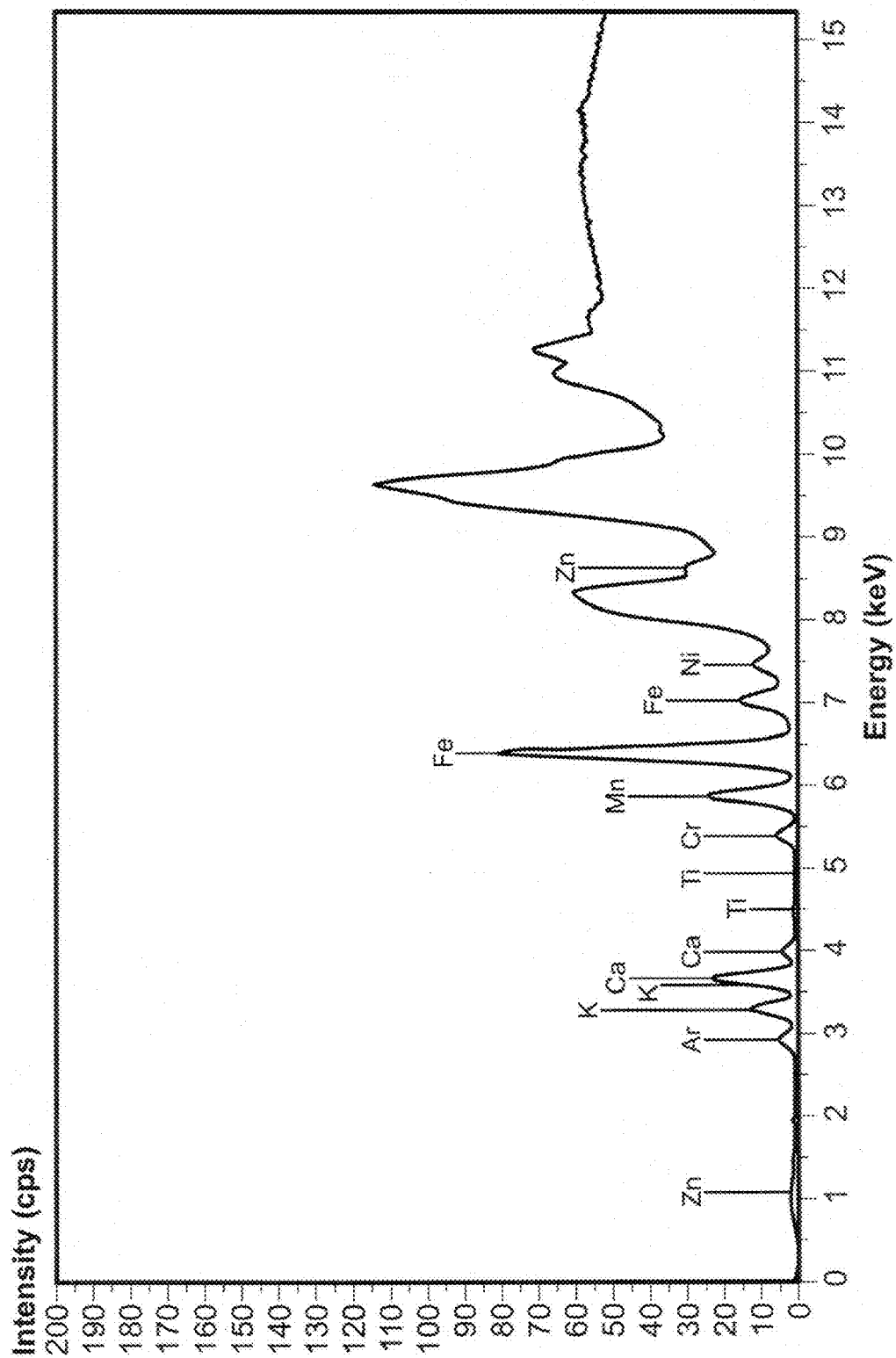
FIGS. 7a and 7b show XRF data of BMF char from red fir and corn cob, respectively.
Figure 7B:
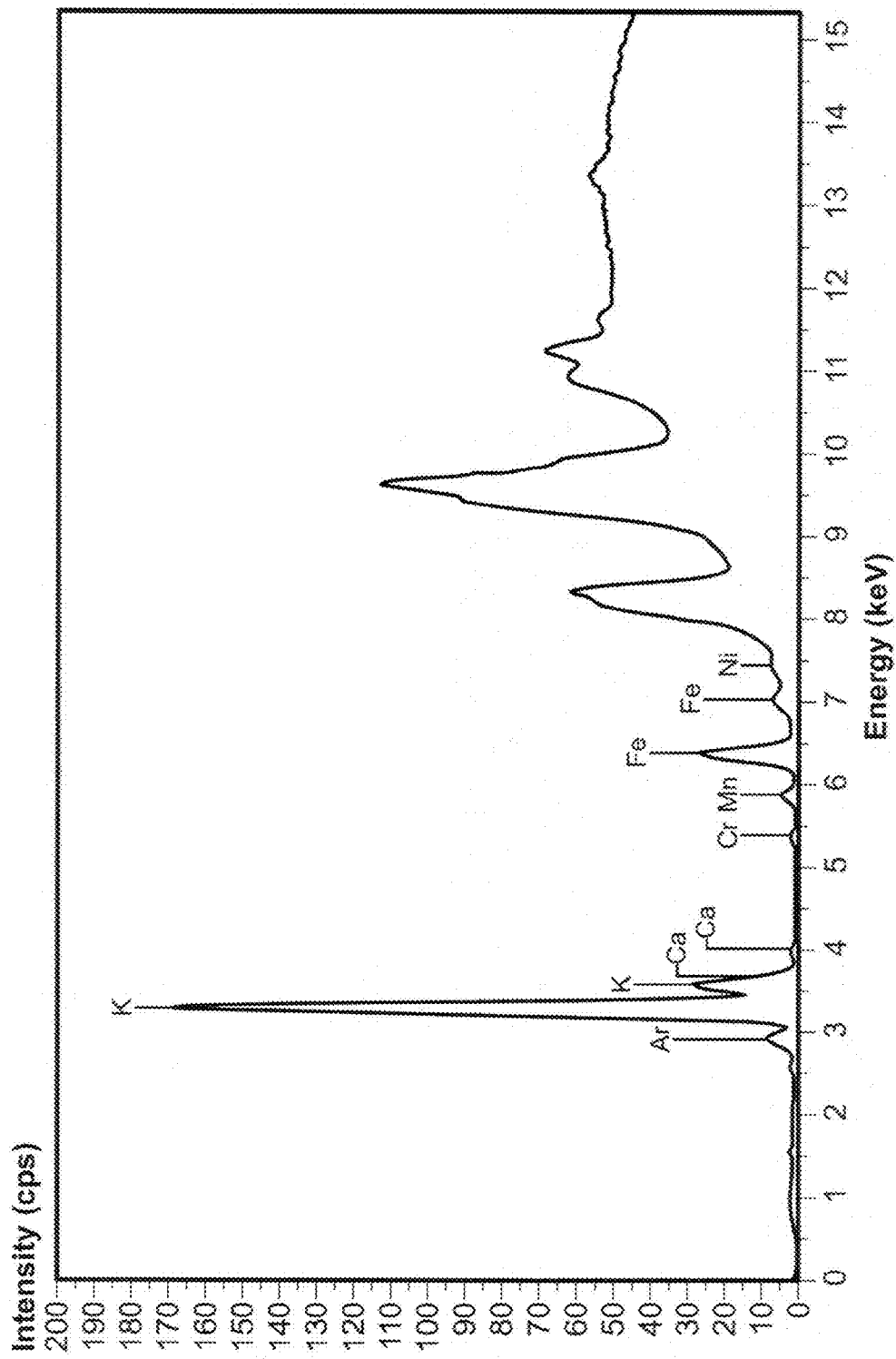

FIGS. 7a and 7b demonstrate an X-ray fluorescence spectra of BMF char from 2 different sources, specifically red fir and corn cobs. The data demonstrates a scan up to 15 keV. If sulfur were present in significant amounts, it would be evident at around 2.2 keV. It is clear for both sources that although the mineral distribution varies between the two, sulfur is not present above background levels. Most of the peaks above 8 keV are background chamber peaks and are not labeled.

Equation 1a evinces that carbon atoms from methane decomposition add a fresh layer to the BMF char surface. Any impurities in the methane feedstock, such as sulfur-based impurities, will tend to be buried in underlying high surface area char surface and eventually accumulate in the ash. The methane may be derived from a number of sources, including stranded gas and wet gas. This process is thus inherently resistant to impurities, but still able to produce high purity synthesis gas. The ability to add oxygen or water ensures that the BMF char surface remains active, as long as the CO removal rate is greater than the carbon deposition rate from the methane reaction. The BMF char can thus be considered to act as a sacrificial catalyst in that it is not consumed in the overall reaction, but does react sacrificially during intermediate stages.

The oxygen in the above reactions may economically be obtained from an air stream. It may also be obtained from a gas that comprises oxygen with a different concentration, such as gas containing pure oxygen, or gas obtained from the decomposition of an oxygen carrying species such as $N_2O$, $H_2O$, $H_2O_2$ or alcohols.

Figure 8A:
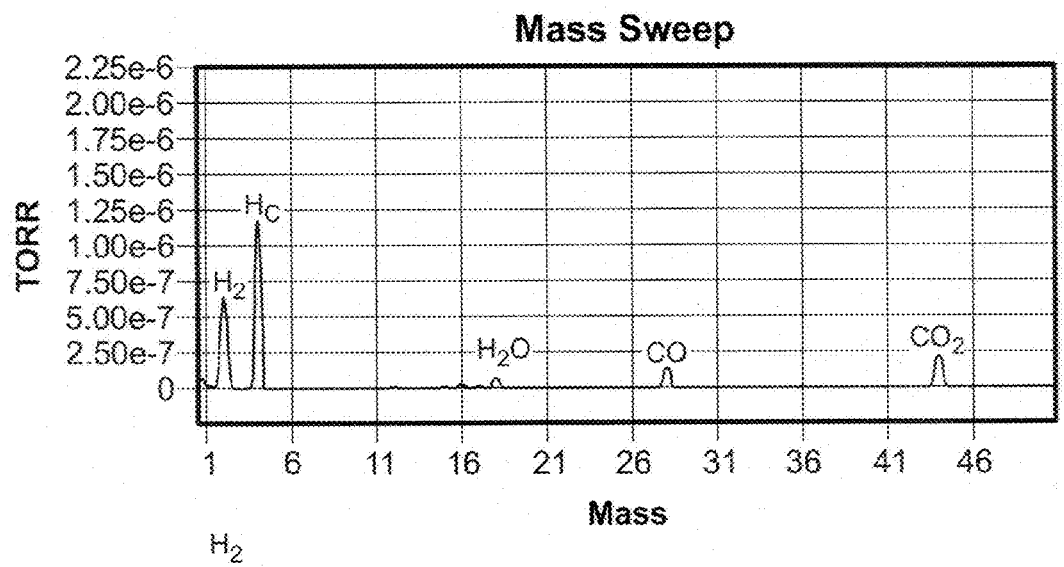
FIGS. 8a-8d show mass spectrometry data for reaction products of BMF char with different reactants.
Figure 8B:
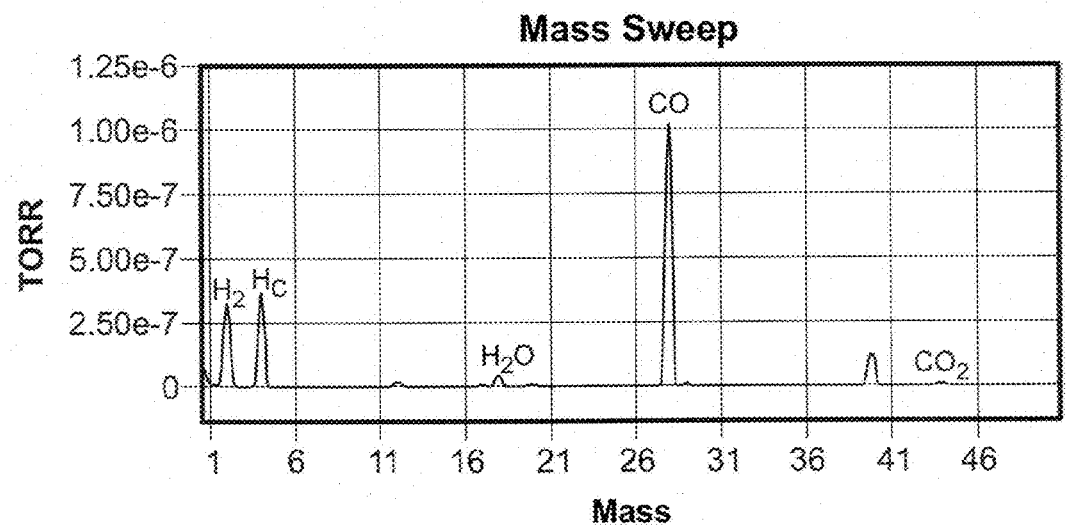
Figure 8C:
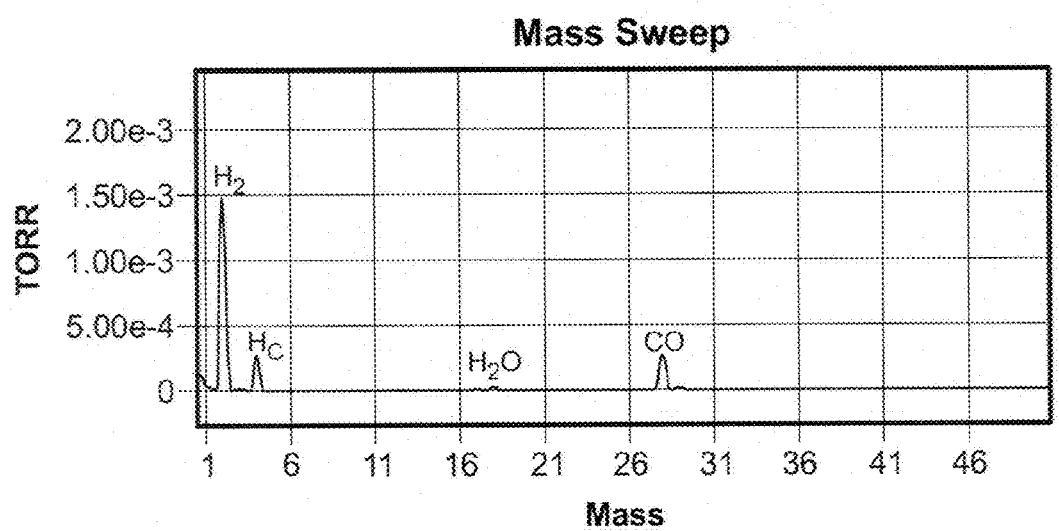

FIG. 8a shows a background mass spectrum of a helium gas stream after it has been exposed to BMF char of the present invention at 900° C. It is shown that background levels of hydrogen (mass 2) are around $6 \times 10^{-7}$ Torr and the background levels of carbon monoxide/nitrogen are $1 \times 10^{-7}$. Some outgassing is evident in the detectable background level of carbon dioxide (mass 44) at $2 \times 10^{-7}$ Torr. FIG. 8b demonstrates results after oxygen in a helium carrier is passed through the BMF char at the same temperature. The mass spectrum of the exit gas demonstrates a major production of CO along with a minor component of carbon dioxide. FIG. 8c shows the results after steam in a helium carrier is reacted with the BMF char at the same temperature. As expected, synthesis gas is produced, as demonstrated in several orders of magnitude increase in hydrogen and carbon monoxide levels above background.

Any one combination of $CH_4$, $H_2O$, $CO_2$ and $O_2$ may be also be used to react with the BMF char to create synthesis gas reaction products, including oxygenates such as aldehydes, ethers, esters, alcohols, and carboxylates. The following lists the possible combinations in relation to reactions involving BMF char and a methane stream:

$$C + CH_4 + O_2$$

$$C + CH_4 + H_2O$$

$$C + CH_4 + CO_2$$

$$C + CH_4 + H_2O + O_2$$

$$C + CH_4 + CO_2 + O_2$$

$$C + CH_4 + H_2O + CO_2$$

$$C + CH_4 + O_2 + H_2O + CO_2$$

Figure 8D:
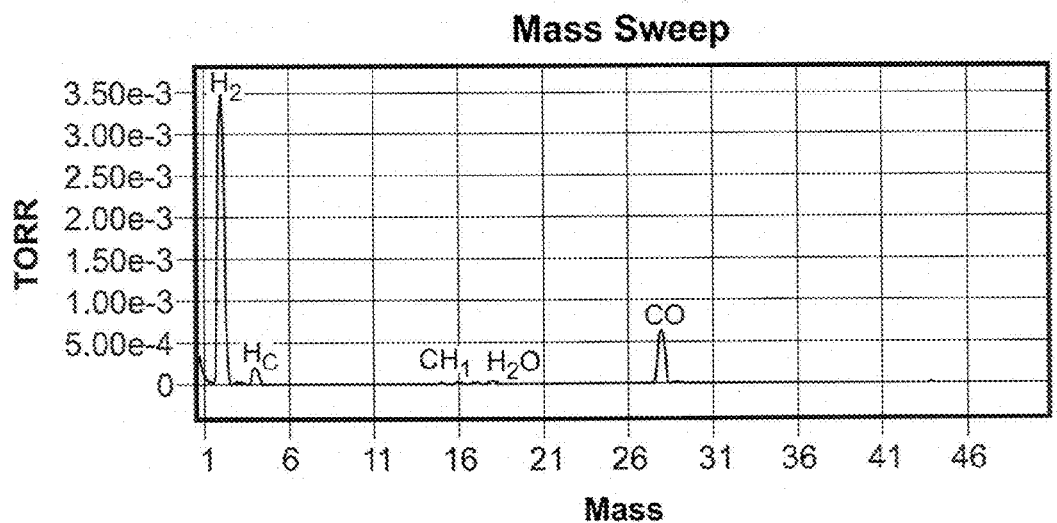

In these cases, proper channeling of reactants is required to minimize formation of carbon dioxide as given in equations 6 and 7. FIG. 8d demonstrates the results after a mixture of methane and water in a helium carrier is reacted with the BMF char at 900° C. Increased levels of synthesis gas were observed as compared with water alone.

The preferred temperature range for the BMF char reactions listed above is in the range of 800° C. to 1100° C., and most preferably 850° C. to 1050° C. The synthesis gas produced is used in process 55 for a wide variety of purposes. It may be converted into oxygenates and hydrocarbons via a number of different catalytic processes, including methanol synthesis processes, Fischer-Tropsch chemistry, and synthesis gas fermentation. The synthesis gas may also be directly combusted. The hydrogen may be separated from the carbon monoxide and used as feedstock for the ammonia synthesis process or as a reactant in fuel cells. The BMF char may also be combined at any stage after its formation with typical chars.

Adjustment of H2/CO Ratio in BMF Char Reactions

The reactions above may occur concurrently or sequentially in one or several reactors. It is understood that best practice entails careful monitoring of reactant concentrations and of reaction products to adjust the output ratios of hydrogen to carbon monoxide. It should be noted that there is no catalyst involved as typical processes that rely on water gas shift catalysts. The BMF char is a sacrificial agent for the ultimate production of hydrocarbons, in essence representing a more efficient use of the biomass. Temperature, pressure and space velocity will affect the results and distribution of synthesis gas products. The hydrogen to carbon monoxide ratio can be varied depending on the nature of feedstock and quantity of material. Indeed, a stream can be engineered to produce a stream comprising of 100% hydrogen, or one of 100% carbon monoxide, or any compositional mixture of the two. Thus a feedstock comprised exclusively of methane can provide a source of pure hydrogen, while a feedstock comprised of oxygen can provide a source of pure carbon monoxide. The two sources can then be mixed in any ratio. A $H_2/CO$ 2:1 ratio is preferable for the methanol production while dimethyl ether requires a 1:1 ratio.

Another method of adjusting ratio is to utilize a wider range of reactants. A wide range of H2/CO ratios can be obtained from using different combinations of reactants, chosen from methane, oxygen, water and carbon dioxide. The actual ratios will depend on the chemical equilibrium of all species, which is determined by temperature, pressure, and concentration of reactants and products. As mentioned above, energy for some of the BMF char reactions can be derived either from external or internal sources. External sources refer to energy supplied in the form of recycled waste heat, or waste heat or electricity coming from outside the system described by the present invention. Internal sources refer to energy channeled from the exothermic reactions, such as shown in equations [4] and [5].

Thermal management via internal energy sources may be achieved with the appropriate combination of reactants to render the synthesis gas formation close to energy neutral.

Modifications may be made by those skilled in the art without affecting the scope of the invention.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. These illustrations and their accompanying description should not be construed as mandating a particular architecture or configuration.

The invention claimed is:

1. A method for producing synthesis gas from biomass, comprising:
   dispensing biomass particles into sheets;
   subjecting the sheets of biomass to a treatment including sequential ramps of temperature followed by pressure shocks, or pressure shocks concurrent with ramps of temperature; and
   recovering a residual non-volatile biomass component from the treatment and reacting the component with at least one of methane, oxygen, steam, and carbon dioxide, at high temperatures.

2. The method of claim 1, wherein the biomass particles have a diameter in the range of 0.001 inch to 1 inch, and wherein the sheets have a thickness that is a multiple of the biomass particle diameter.

3. The method of claim 2, wherein the thickness of the sheets is between 1 and 30 times the biomass particle diameter.

4. The method of claim 1, wherein the ramps of temperature vary from about 0.001° C./sec to about 1000° C./sec.

5. The method of claim 4, wherein the ramps of temperature are varied over a period of time ranging from about 1 microsecond to about 1 week.

6. The method of claim 1, wherein the pressure shocks are incremented over a range of pressures.

7. The method of claim 1, wherein the pressure shocks are applied over a range of times varying from about 1 microsecond to about 1 week.

8. The method of claim 1, wherein the pressure shocks vary in magnitude from about 0.2 MPa to about 10 GPa.

9. The method of claim 8, wherein an admixture of pressure shocks of differing magnitudes are applied over a range of times.

10. The method of claim 1, wherein the biomass is subjected to a controlled gas atmosphere or supercritical fluid while being subjected to a temperature ramp.

11. The method of claim 1, wherein the biomass is subjected to a controlled gas atmosphere or supercritical fluid while being subjected to pressure shocks.

12. The method of claim 1, wherein at least one collected gas component is from the group consisting of: lipids, furans, hydrocarbons or hydrocarbon fragments, and synthesis gas.

13. The method of claim 1, wherein the temperature ramps include a sufficiently high temperature to create a non-volatile carbonaceous material from the biomass.

14. The method of claim 13, wherein the temperature is above 300° C.

15. The method of claim 1, wherein the pressure shocks increase thermal conductivity of formed non-volatile carbonaceous material within the biomass.

16. The method of claim 1, wherein the non-volatile biomass component reacts sacrificially with methane.

17. The method of claim 16, wherein the methane is derived from a wet gas source.

18. The method of claim 1, wherein the reactant comprises oxygen and the oxygen is pure oxygen, part of a mixture of oxygen and an inert agent, or is derived from the decomposition of an oxygen-containing species, selected from the group consisting of: $H_2O$, $H_2O_2$, and $N_2O$.

19. The method of claim 1, wherein the non-volatile component is activated prior to executing synthesis gas generation reactions.

20. A method for adjusting the ratio of hydrogen to carbon monoxide in synthesis gas, comprising:
- dispensing biomass particles into sheets having a thickness that is a multiple of the biomass particle diameter;
- subjecting the sheets of biomass particles to a treatment including sequential ramps of temperature followed by pressure shocks, or pressure shocks and concurrent with ramps of temperature;
- selectively collecting at least one of various groups of volatile compounds as they are released from the biomass;
- collecting a remaining non-volatile component of the sheets;
- reacting the non-volatile component with one of oxygen, methane, steam, and carbon dioxide; and
- adjusting a ratio of reacted oxygen, methane, steam, or carbon dioxide to the non-volatile component to produce synthesis gas having a hydrogen/carbon ratio in a range of 0 to 100.

* * * * *